United States Patent [19]

November

[11] 4,283,936
[45] Aug. 18, 1981

[54] VIBRATION DENSITOMETER ASSEMBLY

[75] Inventor: Milton H. November, Hacienda Heights, Calif.

[73] Assignee: International Telephone and Telegraph Corporation, New York, N.Y.

[21] Appl. No.: 131,387

[22] Filed: Mar. 17, 1980

[51] Int. Cl.[3] ............................................. G01N 9/00
[52] U.S. Cl. .................................................. 73/32 A
[58] Field of Search ....................... 73/32 R, 32 A, 30

[56] References Cited

U.S. PATENT DOCUMENTS 4,064,739  12/1977  November et al. ................ 73/32 A Primary Examiner—James J. Gill
Attorney, Agent, or Firm—A. Donald Stolzy

[57] ABSTRACT

A vibration densitometer probe assembly including a web partly covering a bore in an annular support, the web having a central hole therethrough, a probe shaft sealed through the hole, and a compressed packing in the bore bearing upon the probe shaft.

2 Claims, 4 Drawing Figures

VIBRATION DENSITOMETER ASSEMBLY

BACKGROUND OF THE INVENTION

This invention relates to densitometers, and more particularly to a vibration densitometer probe assembly.

A web supporting an elongate densitometer probe will normally reduce its accuracy and range, and/or increase calculation requirements for the same accuracy.

SUMMARY OF THE INVENTION

In accordance with the present invention, the above-described and other disadvantages of the prior art are overcome by providing a packing to brace the probe.

BRIEF DESCRIPTION OF THE DRAWINGS

In the accompanying drawings which illustrate exemplary embodiments of the present invention.

DESCRIPTION OF THE PREFERRED EMBODIMENT

Figure 1:
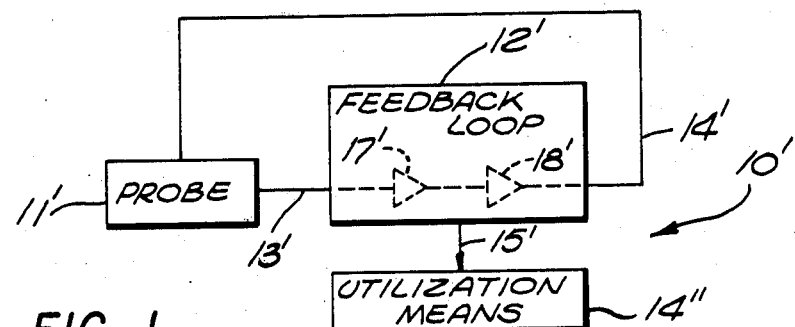
FIG. 1 is a block diagram of a conventional densitometer.

In FIG. 1, a vibration densitometer 10' is shown including a probe 11', a feedback loop 12' connected from and to probe 11' via leads 13' and 14', respectively, and utilization means 14" connected from another output 15' of loop 12'. Densitometer 10' may be identical, if desired, to that disclosed in U.S. Pat. No. 3,677,067, issued July 18, 1972. Attention is also invited to U.S. Pat. No. 3,741,000, issued June 26, 1973, and to U.S. Pat. No. 4,037,460, issued July 26, 1977. By this reference hereto, the entire contents of all of these patents are incorporated herein in their entireties. The same is true of copending application Ser. No. 004,179, filed Jan. 17, 1979, by M. H. November for Densitometer Calibration Method and assigned to the assignee of this application, now U.S. Pat. No. 4,194,385.

Figure 2:
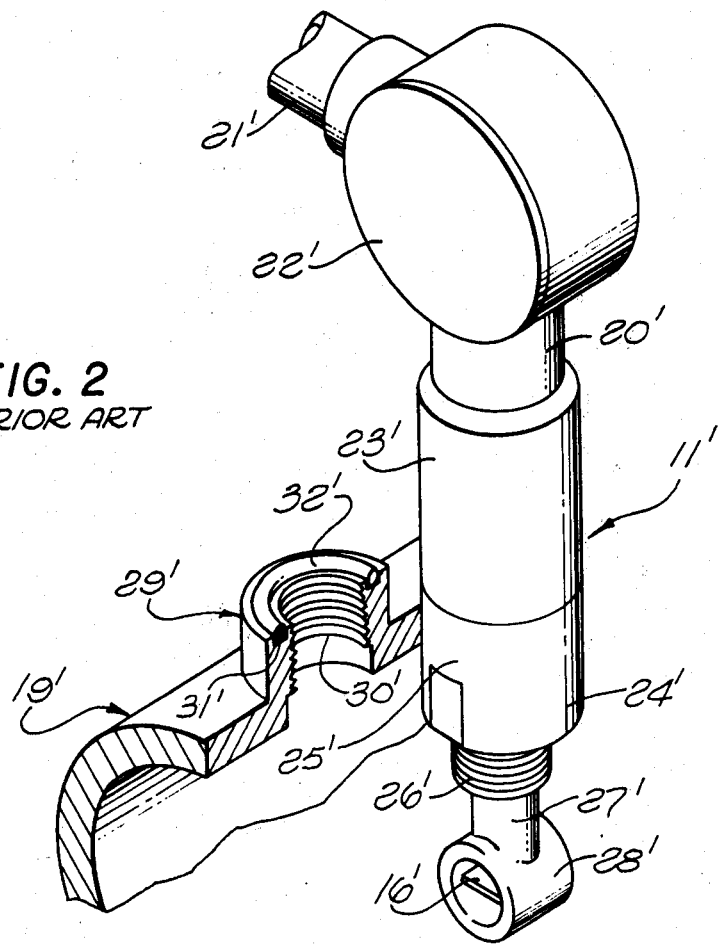
FIG. 2 is a perspective view of a conventional densitometer probe and a pipeline.

Probe 11' contains a vane 16' shown in FIG. 2 which is vibrated. Vane 16' is vibrated because the probe has a piezoelectric crystal pickup, not shown, the output of which is amplified and the vane 16' vibrated by a magnetostrictive driver, not shown. The resonant vibrational frequency f of vane 16' is a known function of the density of the gas or liquid or other fluid in which the vane 16' is immersed.

If desired, loop 12' in FIG. 1 may have a linearization circuit so that the output signal on lead 15' may have a magnitude directly proportional to density.

Utilization means 14" may be a voltmeter or ammeter calibrated in density, a process controller, a gas flow computer, a net oil computer, or otherwise.

In accordance with the foregoing, the word "densitometer" is hereby defined to include or not include utilization means 14". Note will be taken that the densitometer in many cases will be manufactured and sold without any utilization means 14". Such utilization means 14" would be supplied by the customer.

The vibration densitometer 10' is essentially an electromechanical oscillator. The oscillator obviously has losses. Loop 12', therefore, includes at least one amplifier. Two amplifiers 17' and 18' are illustrated in loop 12' in FIG. 1.

Probe 11' is shown again in FIG. 2 for mounting in a pipeline 19'.

Densitometer 10' may, alternatively, be identical, if desired, to that disclosed in said U.S. Pat. No. 3,741,000.

The probe 11' may be identical to the probe shown in the said U.S. Pat. No. 3,741,000, or with certain exceptions.

The probe 11' has conduits 20' and 21', and a pull box 22'. Conduits 20' and 21' and pull box 22' simply serve as enclosures for the output leads from probe 11' to loop 12' shown in FIG. 1.

Conduit 21' is threaded to pull box 22' in a manner not shown. Conduit 20' is threaded to pull box 22' and to a body 23' of probe 11'. Conduits 20' and 21', pull box 22' and body 23' are, thus, all fixed together. A body 24' is fixed to body 23'. Body 24' has an upper portion 25' of a larger diameter and a threaded portion 26' of a smaller diameter that is externally threaded. A shank 27' is fixed to threaded portion 26' and to a cylinder 28'. Vane 16' is mounted in a fixed position along its opposite edges to cylinder 28'.

Pipeline 19' has a hollow cylindrical projection 29' permitting probe 11' to be threaded and lowered thereinto, projection 29' having an axis perpendicular to the axis of pipeline 19'. Projection 29' is internally threaded at 30'. Probe portion 26' is threaded into projection 29' at the thread 30'. Projection 29' has an O-ring groove 31', and an O-ring 32' therein that seals with a shoulder, not visible in FIG. 2, at the bottom of body 24' where the diameter of the probe is reduced to the diameter of the threaded portion 26' thereof. The bottom surface of the body 24' may be flat and in a plane perpendicular to the vertical axis of the probe 11' so as to rest on 0-ring 32', O-ring 32' thereby sealing probe 11' inside pipeline 19'. At least that portion of probe 11' below the thread 26', thus, protrudes downwardly inside pipeline 19' below the inside diameter thereof.

All of the structures shown in FIGS. 1 and 2 may be entirely conventional, if desired.

Figure 3:
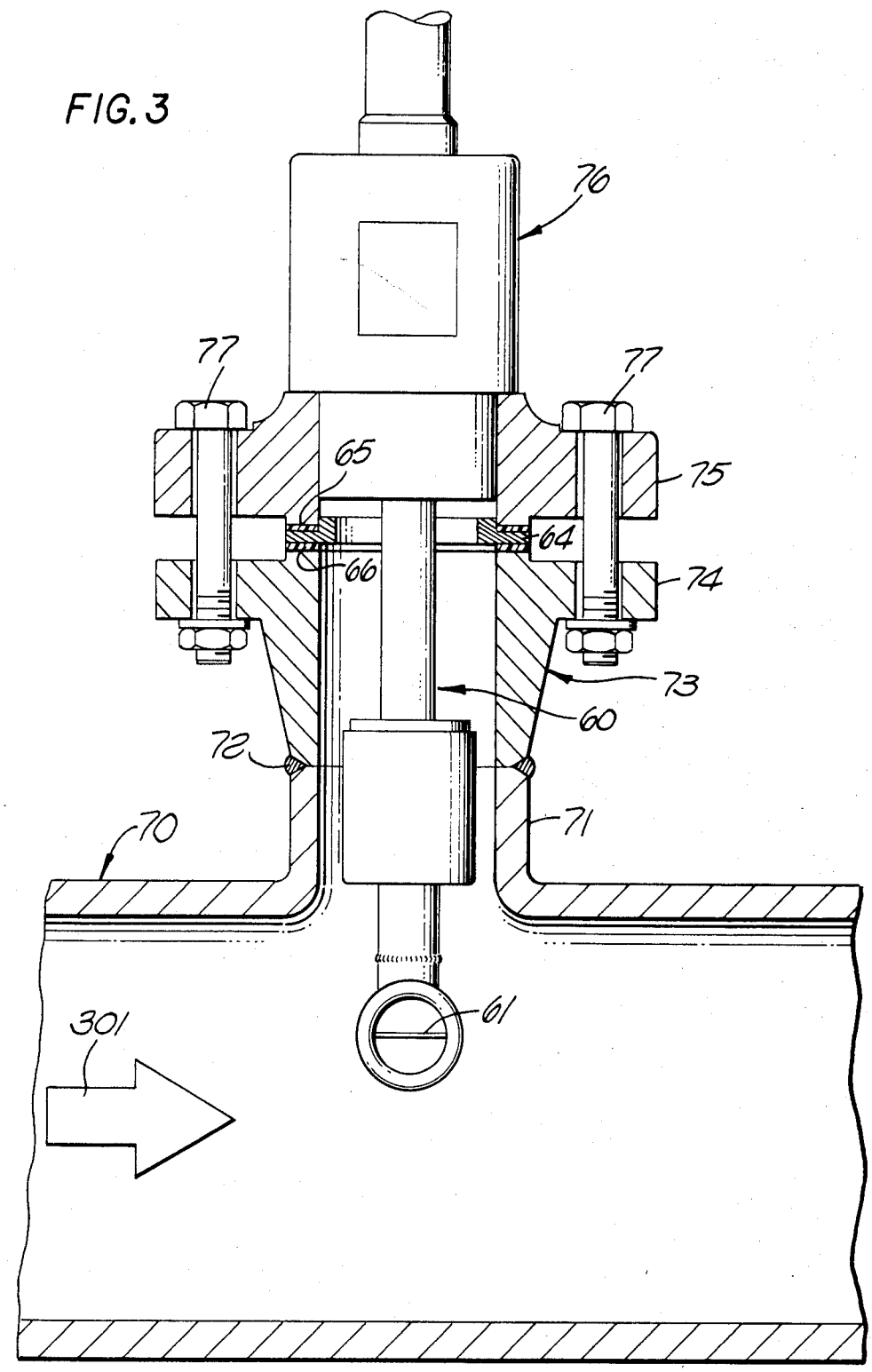
FIG. 3 is a vertical sectional view, partly in elevation, through a pipeline having a vibration densitometer probe mounted in accordance with the present invention.

One embodiment of the present invention is illustrated in FIG. 3. A densitometer probe 60 is shown in FIG. 3 including a vane 61. A ring 64 has annular gaskets 65 annd 66 bonded onto opposite sides thereof.

Fluid flow is in the direction of an arrow 301.

A pipeline is illustrated at 70 having a hollow cylindrical projection 71 which is welded at 72 to a fitting 73 that has a flange 74 bolted to a flange 75 of an assembly 76 at preferably three or more or, for example, eight places 77.

Figure 4:
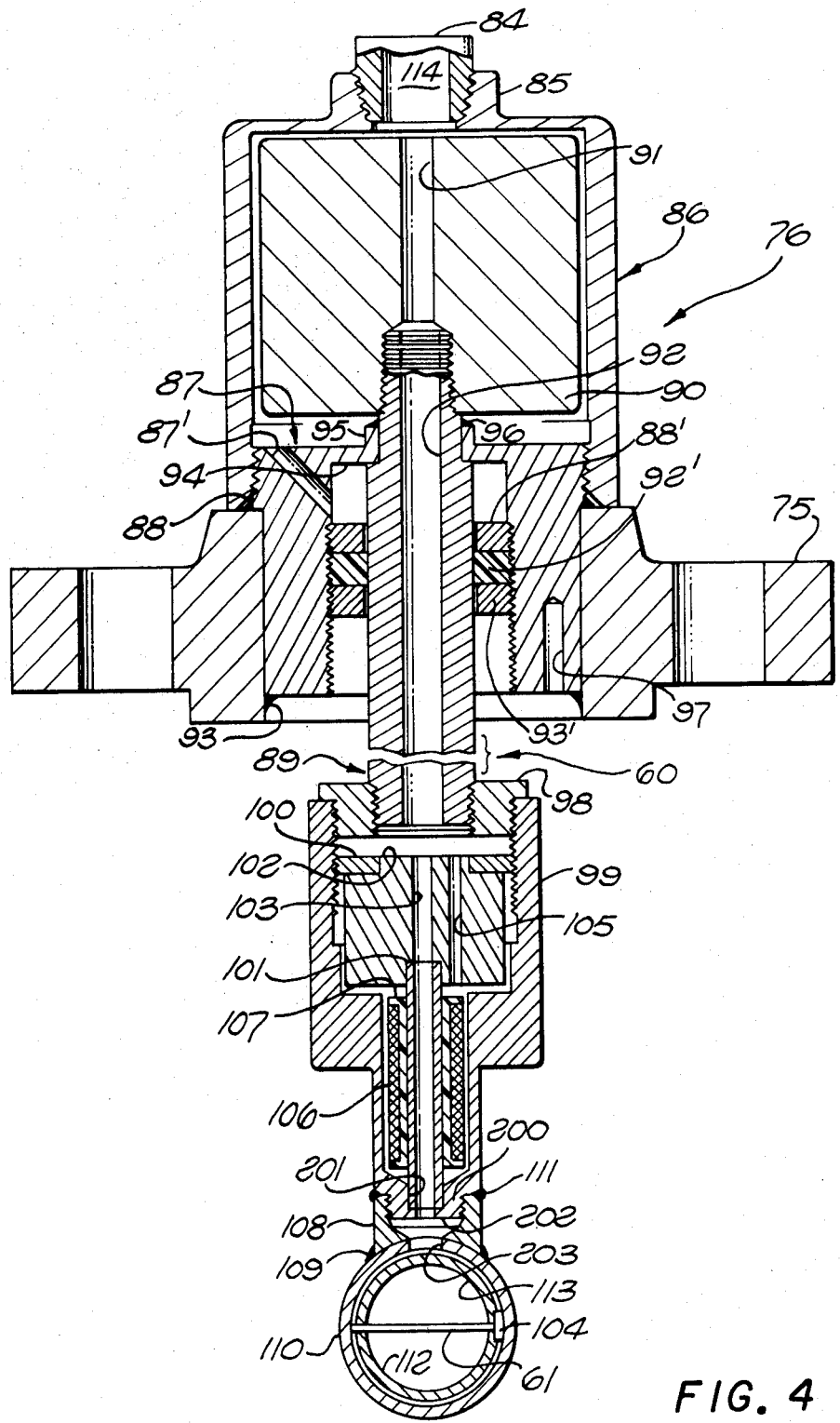
FIG. 4 is a vertical sectional view of a densitometer probe constructed for use in accordance with the present invention.

A vertical sectional view of probe 60 is shown in FIG. 4 where assembly 76 includes a nipple 84 threaded into a hollow cylindrical projection 85 of an end cap 86. End cap 86 is threaded to a body 87. Flange 75, end cap 86 and body 87 are welded or soldered together at 88. A hollow shaft 89 is externally threaded into a cylinder 90 and may be welded thereto, if desired. Cylinder 90 is solid except for a hole 91 which extends completely therethrough and is in communication with the hollow interior 92 of shaft 89. Body 87 is welded at 93 to flange 75, and is provided with a thin web 94 which has an upwardly extending cylindrical projection 95 that is welded at 96 to shaft 89 and to cylinder 90. Body 87 may be provided with a pinhole 97, if desired, so that it may be held while end cap 86 is turned or threaded thereto.

Shaft 89 is, in turn, fixed to a ferrule 98 by being threaded thereinto. Ferrule 98, in turn, is fixed to a body 99 by being threaded thereinto and also welded thereto, if desired.

A ring 100 is threaded into body 99. A magnetostrictive tube 101 which is hollow and open at both ends is press fit into a body 102 and press fit into the lower end 200 of body 99. Body 102 is similar to a body disclosed in the U.S. Pat. No. 3,741,000, issued June 26, 1973, and may be identical thereto, if desired. Alternatively, body 102 may have one hole 103 to receive lead wires from a piezoelectric crystal 104, and a hole 105 to receive lead wires from a drive coil 106 wound on a dielectric spool 107 press fit onto tube 101. A ferrule 108 is welded at 109 to a cylinder 110. Body 99 is threaded into ferrule 108 and welded thereto at 111. Tube 101 extends at the bottom thereof, through a circular hole 201 in the end 200 of body 99. Bore 201 has a shoulder 202 that the lower end of tube 101 abuts.

Cylinder 110 has a circular hole 203 therethrough.

A Vane 61 is fixed inside cylinder 110 in a manner identical to that illustrated in the U.S. Pat. No. 3,677,067, issued July 18, 1972. The same is true of crystal 104.

The utility of a vibration densitometer employing the structure disclosed herein is described in detail in the said patents.

Cylinders 110 and 112, vane 61, and crystal 104 may be identical to those disclosed in the last mentioned patent, if desired.

A more detailed explanation of the operation of a vibration densitometer employing the structure disclosed herein is set forth in the said patents.

It is common to use a preamplifier in the probe. Such a preamplifier may be employed at 114 in FIG. 4, or at any other convenient location, as desired.

When probe 60 is used in the system of either one of the said patents, the system may be constructed so that utilization means 14" (FIG. 1) can be an indicator which will read in pounds per cubic foot, for example.

In accordance with the present invention, in FIG. 4, packing ring 92' is squeezed between body 87 and shaft 89 by annular rings 88' and 93' threaded into body 87. Shaft 89 is thus braced. The space is then vented via hole 87!

What is claimed is:

1. A vibration densitometer assembly comprising: an annular support having a web fixed thereto partly covering a bore and defining a central hole; a vibration densitometer probe having a cylinder sealed to said web through said hole, said cylinder extending into said bore; an annular packing positioned around said cylinder axially spaced from said web, but radially compressed against said cylinder, said packing being squeezed between said bore and said cylinder to hold said cylinder in a bracing position, said packing, said bore, said cylinder and said web defining an annular space, said annular support having a vent hole therethrough extending from said annular space to a point exterior of said annular support.

2. The invention as defined in claim 1, wherein two washer-shaped rings are provided, said rings being threaded into said bore on opposite sides of said packing in a manner to squeeze said packing as aforesaid.

* * * * *